United States Patent [19]
Scholl et al.

[11] Patent Number: 5,071,874
[45] Date of Patent: Dec. 10, 1991

[54] L-CARNITINE MAGNESIUM CITRATE

[75] Inventors: Thomas Scholl, Visp; Willibald F. Kohl, Muri bei Bern, both of Switzerland

[73] Assignee: Lonza Ltd., Gampel/Valais, Switzerland

[21] Appl. No.: 537,989

[22] Filed: Jun. 13, 1990

[30] Foreign Application Priority Data

Jun. 14, 1989 [CH] Switzerland ............ 2221/89

[51] Int. Cl.$^5$ .............................................. A61K 31/205
[52] U.S. Cl. .................................... 514/561; 514/574; 562/567; 562/584; 426/72
[58] Field of Search ............... 514/561, 574; 562/567, 562/584; 428/72

[56] References Cited

U.S. PATENT DOCUMENTS

| 3,810,994 | 5/1974 | Wiegand | 424/316 |
| 4,172,072 | 10/1979 | Ashmead | 562/567 |
| 4,255,449 | 3/1981 | Cavazza | 424/316 |
| 4,371,618 | 2/1983 | Cavazza | 435/128 |
| 4,537,772 | 8/1985 | Alexander et al. | 514/9 |
| 4,602,039 | 7/1986 | Cavazza | 562/567 |
| 4,806,282 | 2/1989 | Tinti et al. | 260/501 |
| 4,855,289 | 8/1989 | Wester et al. | 514/561 |
| 4,871,550 | 10/1989 | Millman | 514/561 |
| 4,883,786 | 11/1989 | Puricelli | 562/567 |
| 4,895,980 | 1/1990 | Walsdorf et al. | 562/585 |

FOREIGN PATENT DOCUMENTS

| 23217 | 4/1962 | Fed. Rep. of Germany . | |
| 38-19995 | 2/1963 | Japan | 562/567 |
| 38-24889 | 6/1963 | Japan | 562/567 |
| 57-126420 | 6/1982 | Japan . | |

OTHER PUBLICATIONS

Greff, Chem. Abst; vol. 112, #25391X (19.
Strack et al., Hoppe-Seyler's Zeitschrift fur Physiologische Chemie, vol. 318, (1960), pp. 129-137.

Primary Examiner—James H. Reamer
Attorney, Agent, or Firm—Fisher, Christen & Sabol

[57] ABSTRACT

L-carnitine magnesium citrate and a process for its production, starting from a magnesium compound, citric acid and L-carnitine, as well as the use of the product as a combination preparation in sports nutrition or as a pharmacological active ingredient.

3 Claims, No Drawings

L-CARNITINE MAGNESIUM CITRATE

BACKGROUND OF THE INVENTION

1. Field of The Invention

The invention relates to L-carnitine magnesium citrate, which is present as a true complex salt, to a process for the production of this compound and to the use of this compound as a combination preparation of carnitine and magnesium in sports nutrition or as a pharmacological active ingredient. This compound has the following formula:

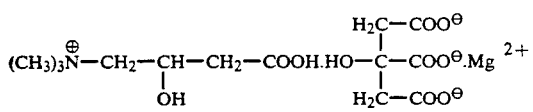

2. Background Art

Both magnesium and L-carnitine are increasingly eliminated during physical training via perspiration or urine. These losses cause:
magnesium or L-carnitine deficiency phenomena
muscle cramps
reduction of efficiency
cardiac irregularities.

It is known that L-carnitine as well as magnesium salts, e.g., magnesium aspartate and magnesium orotate, exhibit high hygroscopicity.

BROAD DESCRIPTION OF THE INVENTION

The main object of the invention is to produce a new derivative of L-carnitine which exhibits slight hygroscopicity and good thermal stability. Other objects and advantages of the invention are set out herein or are obvious herefrom to one skilled in the art. The objects and advantages of the invention are achieved by the compound and processes of the invention.

The invention involves L-carnitine magnesium citrate.

The invention also involves a process for the production of L-carnitine magnesium citrate of the formula:

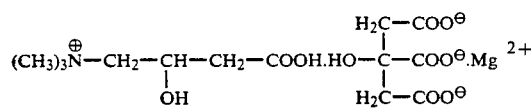

characterized in that a magnesium compound, citric acid and L-carnitine in stoichiometric portions, in a suitable solvent, are converted to the corresponding L-carnitine magnesium citrate and then the L-carnitine magnesium citrate is recovered from the solution. Preferably magnesium citrate (in place of the magnesium compound and the citric acid) and L-carnitine in stoichiometric portions, in a suitable solvent, are converted to the corresponding L-carnitine magnesium citrate and then the L-carnitine magnesium citrate is recovered from the solution. Water is preferably used as the solvent. Magnesium hydroxide, magnesium oxide or magnesium chloride is preferably used as the magnesium compound. Most preferably magnesium hydroxide is used as the magnesium compound. The L-carnitine magnesium citrate is preferably recovered from the solution by evaporation to dryness. The solution is preferably concentrated by evaporation by spray drying. The solution is also preferably concentrated by evaporation on a rotary evaporator. After concentration by evaporation on a rotary evaporator, the L-carnitine magnesium citrate is preferably recrystallized in a mixture of a low-boiling alkyl alcohol with an aliphatic ketone.

The invention also involves the use of L-carnitine magnesium citrate as a combination preparation of carnitine and magnesium in the field of sports nutrition. The invention further involves the use of L-carnitine magnesium citrate as a pharmacological active ingredient.

DETAILED DESCRIPTION OF THE INVENTION

The process for the production of L-carnitine magnesium citrate can be performed according to the invention from stoichiometric portions of a magnesium compound, citric acid and L-carnitine, in a suitable solvent, such as, water, methanol and ethanol. Preferably the reaction is performed in an aqueous medium. The reaction temperature is suitably 20° to 100° C., preferably 50° to 70° C. Magnesium hydroxide, magnesium oxide and magnesium chloride can be used as the magnesium compound; preferably magnesium hydroxide is used.

According to a preferred variation of the process according to the invention, L-carnitine magnesium citrate can be recovered from magnesium citrate and L-carnitine.

The magnesium citrate salt is obtained if the solvent, after a certain reaction time, is then either spray-dried, vacuum-dried, freeze-dried or concentrated by evaporation on a rotary evaporator; preferably the solution is concentrated by evaporation by spray drying. By spray drying, the desired product is obtained in the desired grain size. Instead of spray drying, the solution can be concentrated by evaporation on a rotary evaporator and the resultant residue further treated by a purification treatment/scheme in a suitable solvent. The residue is suitably taken up in a mixture of a low-boiling alcohol with an aliphatic ketone. Methanol, ethanol, propanol and isopropanol are examples of the alcohol; preferably methanol is used. Acetone and methyl ethyl ketone are examples of the ketone; preferably acetone is used.

The compounds of the invention represent an ideal ratio of L-carnitine and magnesium. The muscle tissue of a healthy adult contains both 20 g of magnesium and 20 g of L-carnitine and can absorb 2 g of L-carnitine and about 300 mg of magnesium for optimal energy supply. A daily dose of 2 to 5 g of L-carnitine magnesium citrate supplies the body with 780 to 1950 mg of L-carnitine and 126 to 315 mg of magnesium. By the synergistic effect of magnesium and L-carnitine, the compound of the invention exhibits the following extraordinary, useful properties:
clearly higher performance and improved endurance in athletes as well as shorter rest periods
balancing of the increased magnesium and L-carnitine demand in competitive sports
delay of fatigue
strengthening of cardiac performance and prevention of cardiac irregularities
increased stress tolerance
less tendency to have muscle and vascular spasms
improvement of muscular activity
increase of the activity of enzyme reactions in energy metabolism.

EXAMPLE

L-carnitine magnesium citrate

A mixture of citric acid (19.3 g, 0.1 mol), magnesium hydroxide (6.1 g, 0.1 mol) and L-carnitine (16.1 g, 0.1 mol) was dissolved in water (50 ml) and stirred for 1 hour at 60° C. By spray drying, 36.0 of product as a fine, light powder, corresponding to a yield of 95 percent (relative to the L-carnitine used), was obtained from the clear solution. The solution was concentrated by evaporation on a rotary evaporator. Then the residue was taken up in a mixture of acetone (100 ml) and methanol (100 ml), then filtered and dried (12 hours at 60° C. and 40 mbars); a coarser powder, corresponding to a yield of 95 percent (relative to the L-carnitine used), was obtained. Data for the product was:

Melting point: over 250°C.

Specific rotation: $[\alpha]^{25}_D[c=1\%$ in $H^2O]-12°(\pm 1)$

Solubility: over 50 g/100 ml of water.

The structure was confirmed by IR, NMR and X-ray spectroscopy. Further data for the product was:

Thermal stability: Externally unchanged after 24 hours in the air at 100° C.

Weight loss: 5%

Hygroscopicity:

| Air moisture, % | 32 | 44 | 56 | 66 | 73 | 80 |
|---|---|---|---|---|---|---|
| Water absorption, % after 1 week | 8 | 15 | 21 | 29 | 35 | 46 |

No deliquescence.

What is claimed is:

1. L-carnitine magnesium citrate.

2. Process comprising using L-carnitine magnesium citrate of the formula:

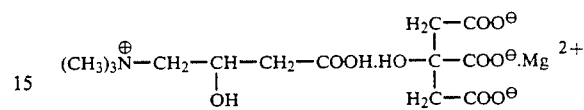

as a combination preparation of carnitine and magnesium in sports nutrition.

3. Process comprising using L-carnitine magnesium citrate of the formula:

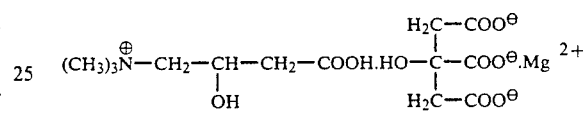

as a pharmacological active ingredient.

* * * * *